United States Patent [19]
Schwarz

[11] Patent Number: 5,952,576
[45] Date of Patent: Sep. 14, 1999

[54] CONCURRENT RUS MEASUREMENTS USING MULTIPLE FREQUENCIES

[75] Inventor: James J. Schwarz, Albuquerque, N.Mex.

[73] Assignee: Quasar International, Albuquerque, N.Mex.

[21] Appl. No.: 08/826,148

[22] Filed: Mar. 27, 1997

[51] Int. Cl.[6] .......................... G01N 29/12; G01N 29/06
[52] U.S. Cl. .................. 73/579; 73/602; 702/36; 702/39
[58] Field of Search ............................. 73/579, 582, 583, 73/602, 659; 364/508; 702/34, 35, 39, 36, 56

[56] References Cited

U.S. PATENT DOCUMENTS

| | | | |
|---|---|---|---|
| 3,659,456 | 5/1972 | Marshall et al. | 73/579 |
| 3,842,661 | 10/1974 | Marshall et al. | 73/579 |
| 4,233,843 | 11/1980 | Thompson et al. | 73/579 |
| 4,669,320 | 6/1987 | Simonsen | 73/862.59 |
| 4,716,764 | 1/1988 | Felix | 73/571 |
| 4,976,148 | 12/1990 | Migliori et al. | 73/579 |
| 5,062,296 | 11/1991 | Migliori | 73/579 |
| 5,351,543 | 10/1994 | Migliori et al. | 73/579 |
| 5,425,272 | 6/1995 | Rhodes et al. | 73/579 |
| 5,495,763 | 3/1996 | Rhodes et al. | 73/579 |

*Primary Examiner*—Thomas P. Noland
*Assistant Examiner*—Rose M. Miller
*Attorney, Agent, or Firm*—Snider & Chao LLP; Ronald R. Snider

[57] ABSTRACT

A part undergoing resonant ultrasound testing is simultaneously driven at a plurality of resonant test frequencies. The response of the part is measured simultaneously. There may be one or more driving transducers and one or more vibration sensing transducers.

5 Claims, 4 Drawing Sheets

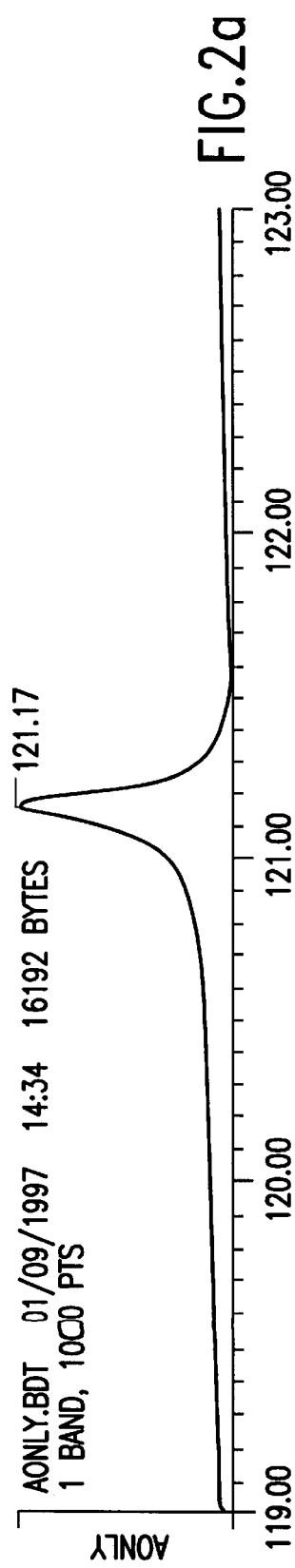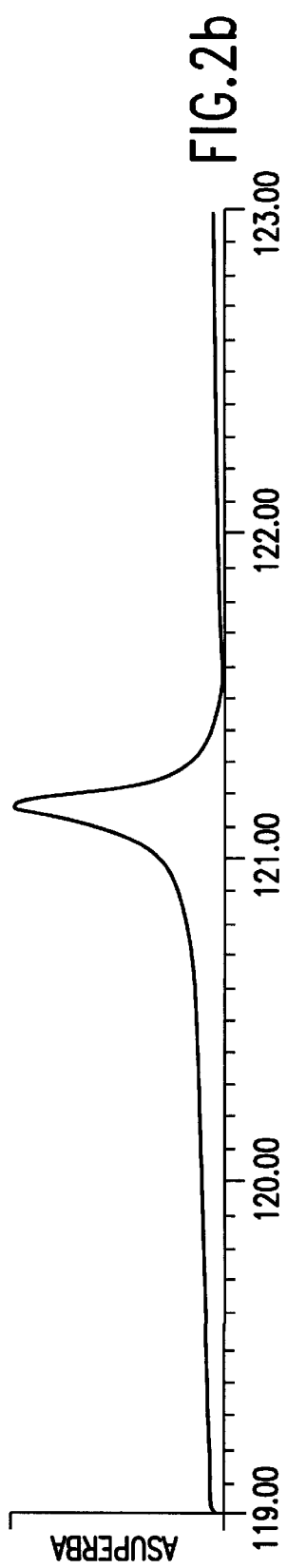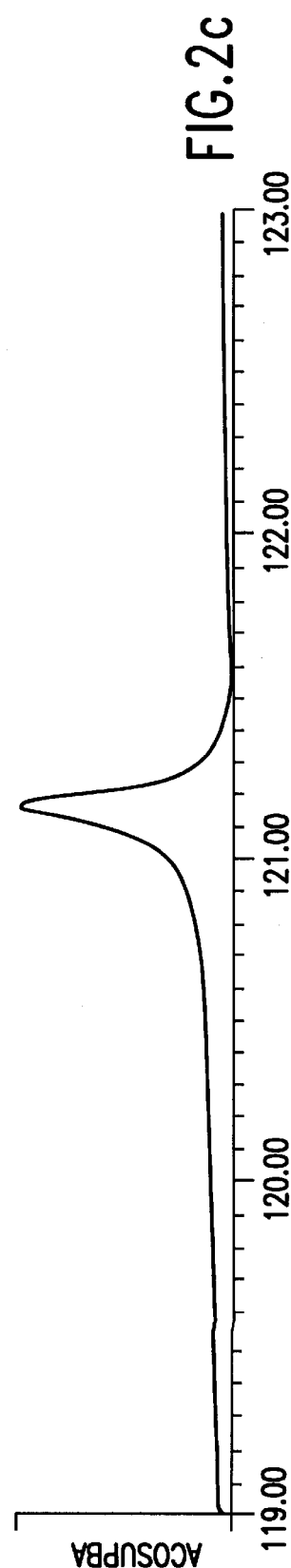

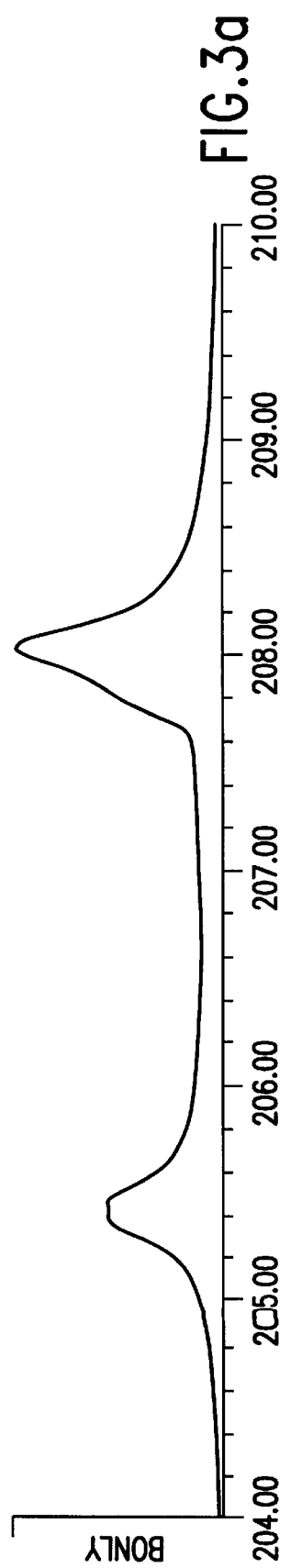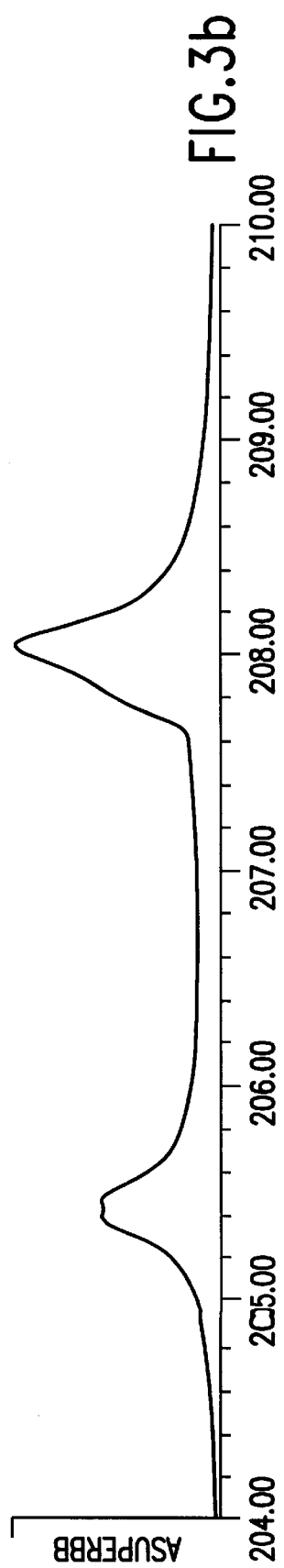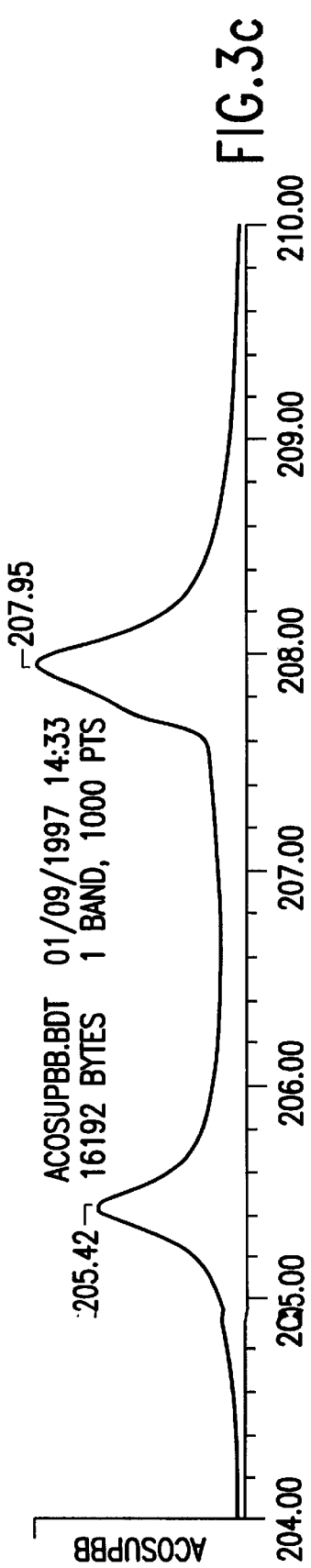

CONCURRENT RUS MEASUREMENTS USING MULTIPLE FREQUENCIES

FIELD OF THE INVENTION

This invention is in the field of Resonant Ultrasound Testing and provides faster testing which results in greater test part throughput.

THE PRIOR ART

Previous patents including U.S. Pat. Nos. 5,351,543; 5,355,731; 5,062,296; 5,425,272; 5,408,880; 5,495,763; and 4,976,148. Disclose methods for detecting defects such as cracks, chips, inclusions or dimensional variations based on Resonant Ultrasound Spectroscopy (RUS). Essentially, this involves measuring the change in the frequency of a mechanical resonance caused by the defect. A complex part may be susceptible to several types of defects and each type of defect can be located in any of several different regions of the part. Each combination of defects type and defects and location of defects may be associated with a different resonance. As a result, a non-destructive RUS test may require measuring 5 to 10 separate resonances.

BRIEF SUMMARY OF THE INVENTION

A method for measuring several resonant frequencies concurrently in order to increase the throughput of a non-destructive test based on Resonant Ultrasound Spectroscopy (RUS) is provided. The part under test is simultaneously driven at two or more resonant frequencies and the steady state response is measured simultaneously.

Each resonance measurement requires a time interval which depends on the frequency of the resonance, the Q of the material and the range of production variation for the part. The time interval is largely a function of the time required for the part to reach a steady state vibrational state. If this time is reduced, the efficiency of the entire process will be greatly improved. Typical RUS measurement times range from 0.1 seconds to 10 seconds per resonance. Since typical production lines have throughputs with similar times, the RUS measurement can be a bottleneck in the production system. This leads to a requirement for multiple RUS units which increases the cost and complexity of the system.

Concurrent resonance measurements provide a method for substantially increasing the throughput of the RUS measurements and thereby reducing the cost and complexity of non-destructive testing.

The RUS technique is a linear process. The part being measured is essentially a linear transfer function relating the frequency generation and detection. When the part is driven by a steady state (CW) frequency, it vibrates only at that frequency. (Under certain conditions, harmonics of the drive frequency can be produced by non-linear reactions, but these have been found not to be significant in most applications.) When the part is driven concurrently by two or more frequencies, it vibrates simultaneously at all of these frequencies. When viewed in the time domain, the net vibration is a complex superposition, in which any specific frequency may not be recognized. However, in the frequency domain, each vibrational frequency maintains its individual identity.

Concurrent or simultaneous resonance measurement by simultaneously driving a part requires several conditions which are:

(1) sufficient measurement time so that steady state vibration exists, i.e., the transient vibrations have decayed;
(2) linear excitation, i.e., drive level low enough to avoid nonlinear excitation of the part or the transducers; and
(3) measurement frequencies separated sufficiently so that filtering is feasible and filtering sufficient to prevent crosstalk between the individual frequencies.

BRIEF DESCRIPTION OF THE DRAWINGS

FIG. 2a shows resonant response of a part driven with a single drive transducer $D_A$ as received by a single receive transducer $R_A$ and received in $RUS_A$ of FIG. 1.

FIG. 2b shows the response of the receiver $RUS_A$ of FIG. 1a when the part is simultaneously driven by a separate transducer $D_B$ at different frequencies which are shown in FIG. 3a.

FIG. 2c shows the response of receiver $RUS_A'$ with the transducer operating simultaneously at frequencies A' and B' in the configuration shown in FIG. 1b.

FIG. 3a shows the response of receiver $RUS_B$ when operating with transducer $D_B$ in FIG. 1a.

FIG. 3b shows the response of receiver $RUS_B$ when operating with simultaneous inputs from transducers $D_A$ and $D_B$ in the configuration of FIG. 1a.

FIG. 3c shows the response of receiver $RUS_B'$ when operating with simultaneous inputs from frequency generators A' and B' in the configuration of FIG. 1b.

DETAILED DESCRIPTION

Applicant has discovered that a part may be driven simultaneously with a plurality of resonant frequencies, and the response thereto measured. Further analysis of the response of the part to the driven frequency can be conducted in accordance with any number of analysis techniques, such as those taught in U.S. Pat. Nos. 5,351,543; 5,355,731; 5,062,296; 5,425,272; 5,408,880; 5,495,763; and 4,976,148.

Figure 1A:
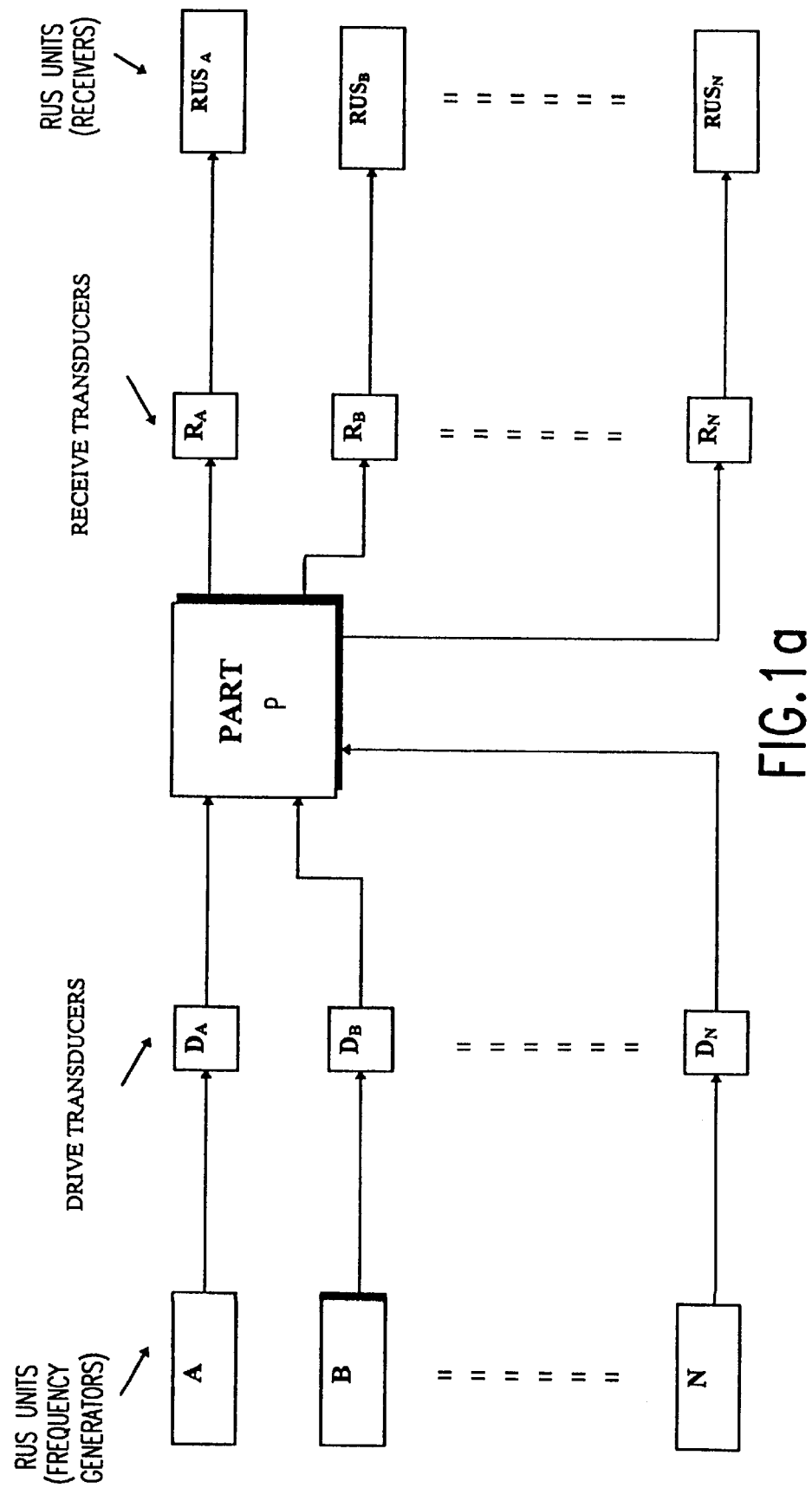
FIG. 1a shows an embodiment of the invention where a plurality of drive transducers are each attached to a part, and a corresponding plurality of receive transducers are in contact with the part.

In the embodiment shown in FIG. 1a, the RUS units (frequency generators) A, B, . . . and . . . N are each used to individually drive transducers $D_A$, $D_B$, . . . $D_N$. The transducers $R_A$, $R_B$ . . . provide inputs to RUS receivers and analyzers $RUS_A$, $RUS_B$ . . . $RUS_N$.

The elements depicted in FIG. 1a are known in the art, and are illustrated in U.S. Pat. Nos. 4,976,148; 5,351,543; 5,408,880; 5,425,272; and 5,062,296, all of which are incorporated herein by reference.

Figure 1B:
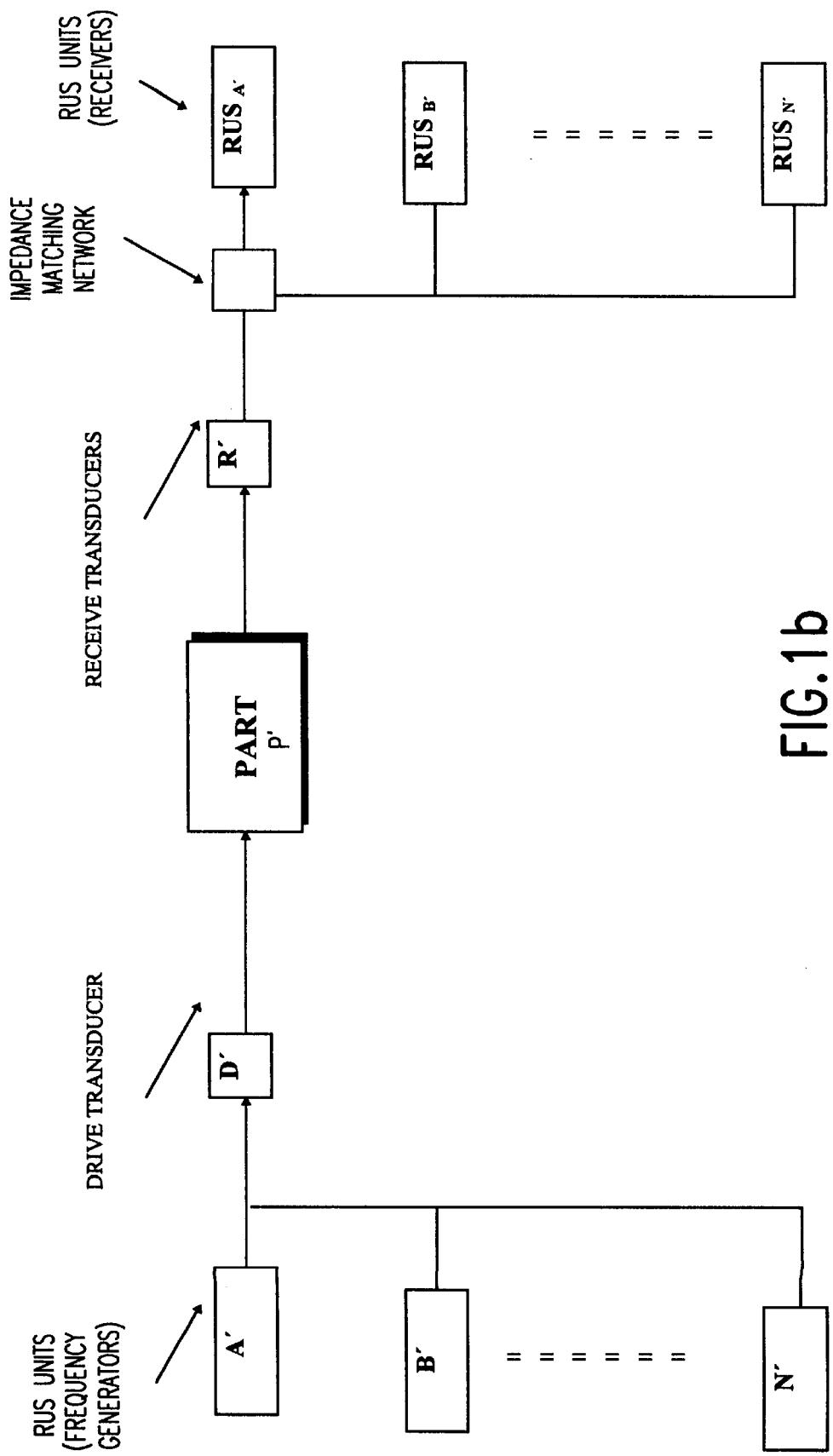
FIG. 1b shows another embodiment of the invention where a plurality of frequencies are applied to a single drive transducer which then drives the part. Similarly, in FIG. 1b, a single receive transducer receives vibrations from the part, and multiple resonant responses are received by a plurality of receivers.

FIG. 1a and 1b show different configurations for concurrent RUS measurements. In FIG. 1a, a separate RUS measurement unit is required for each frequency. A unit similar to that described in U.S. Pat. No. 4,976,148, incorporated herein by reference, is most appropriate, but other types of narrow band frequency generation/detection can be used.

The separate frequencies can excite the part in either of two ways. In the first embodiment (FIG. 1a), separate drive and receive transducer pairs are used for each frequency. The part simultaneously vibrates at all of the frequencies and each RUS unit records its appropriate portion of the spectrum. In the second embodiment (FIG. 1b), the outputs of the individual RUS units are superimposed as inputs; to the drive transducer. Again, the part vibrates at all of the frequencies. Then the receive transducer output is fed to the individual RUS units which record the appropriate portion of the spectrum. Depending on the input impedance of the receivers, an impedance matching network may be required to prevent degradation of the transducer output. Alternately, a separate receive transducer can be used for each RUS unit.

EXPERIMENTAL DEMONSTRATION

The apparatus of FIG. 1a and 1b was used to demonstrate the implementation of the simultaneous driving measurement method. In FIG. 1a, two independent RUS units, A and B, were used. Unit A measured a single resonance across the range 119 Khz to 123 Khz for a ceramic part. Unit B measured two resonances across the range 204 Khz to 210 Khz. The results are shown in FIGS. 2a and 2b which show the measurements for Unit A at receiver $RUS_A$. The curve FIG. 2a is the measurement with only unit $D_A$ of FIG. 1a driving the part. The curve marked FIG. 2b is the measurement at $RUS_A$ with Driving Unit $D_B$ operating simultaneously to driver $D_A$ in the configuration shown in FIG. 1a.

The curve marked FIG. 2c is the $RUS_A$ measurement with inputs A' B' operating simultaneously in the configuration described above as the embodiment of FIG. 1b, with single transmit and receive transducers. As seen in the figures, all three of the resonances are identical. FIGS. 3a, 3b, and 3c present the same data for receivers $RUS_B$ and $RUS_B'$. Again, all of the resonances are identical and therefore show that the simultaneous driving of the part at a plurality of resonant frequencies does not prevent measurement of individual resonant responses.

What is claimed is:

1. A method for measuring multiple resonant frequencies of a manufactured part to determine the presence of defects comprising the steps of:

selecting at least two distinct and seperate frequency ranges for said part, each of which contains at least one predicted prominent resonance;

simultaneously driving said part across each of the selected frequency ranges;

simultaneously measuring prominent responses of said part across said frequency ranges; and determining if the manufactured part contains a defect by analyzing said simultaneously measured prominent responses to predicted prominent responses.

2. The method in accordance with claim 1 wherein separate drive transducers are used for each resonant frequency range.

3. The method in accordance with claim 2 wherein separate receive transducers are used for each resonant frequency range.

4. The method in accordance with claim 2 wherein the number of drive transducers is less than the number of resonant frequency ranges.

5. The method in accordance with claim 2 wherein the number of receive transducers is less than the number of resonant frequency ranges.

* * * * *